United States Patent [19]

Inamori et al.

[11] 4,446,579
[45] May 8, 1984

[54] FLEXIBLE CERAMIC BIO-IMPLANT MEMBER

[75] Inventors: Kazuo Inamori, Kyoto; Masaya Hirabayashi, Yokaichi, both of Japan

[73] Assignee: Kyocera Corporation, Kyoto, Japan

[21] Appl. No.: 369,171

[22] Filed: Apr. 16, 1982

Related U.S. Application Data

[63] Continuation of Ser. No. 100,059, Dec. 4, 1979, abandoned.

[30] Foreign Application Priority Data

Dec. 4, 1978 [JP] Japan .................. 53-150401

[51] Int. Cl.³ .................. A61F 1/24; A61F 5/04; A61B 17/18; A61C 13/30
[52] U.S. Cl. .................. 3/1.91; 3/1.9; 3/1.913; 128/92 C; 128/92 BC; 128/92 CA; 433/173; 433/201
[58] Field of Search .................. 3/1.9, 1.91, 1.913; 128/92 C, 92 CA, 92 BC; 433/201-202, 173, 175

[56] References Cited

U.S. PATENT DOCUMENTS

| 2,210,424 | 8/1940 | Morrison | 433/175 |
| 3,662,405 | 5/1972 | Bortz et al. | 3/1.9 |
| 3,707,006 | 12/1972 | Bokros et al. | 3/1.9 |
| 3,906,550 | 9/1975 | Rostoker et al. | 3/1.913 X |
| 4,230,455 | 10/1980 | Hidaka et al. | 128/92 C X |

FOREIGN PATENT DOCUMENTS 923085  2/1955  Fed. Rep. of Germany ... 128/92 BC

*Primary Examiner*—Ronald L. Frinks
*Attorney, Agent, or Firm*—Spensley, Horn, Jubas & Lubitz

[57] ABSTRACT

The disclosure relates to a flexible ceramic bio-implant member comprising a bundled body of a plurality of ceramic fibers having flexibility and elasticity and bundled into a desired shape in the state of the fibers being allowed to make flexible movement. The bio-implant member is enabled to serve the purpose of flexible reinforcement of a conventional implant member by the use of this flexible bio-implant member in combination with the latter.

14 Claims, 12 Drawing Figures

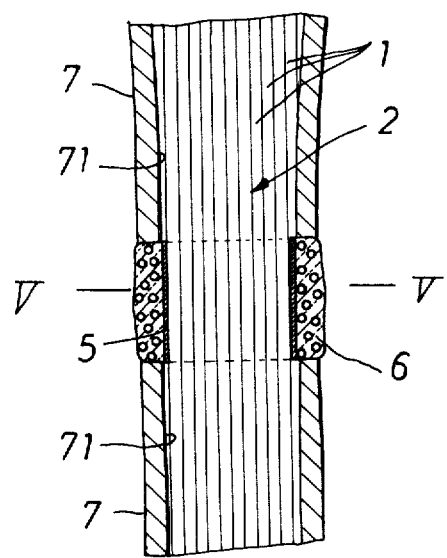
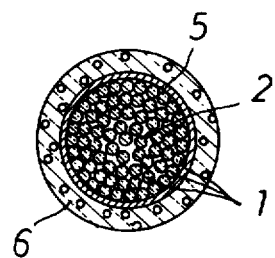

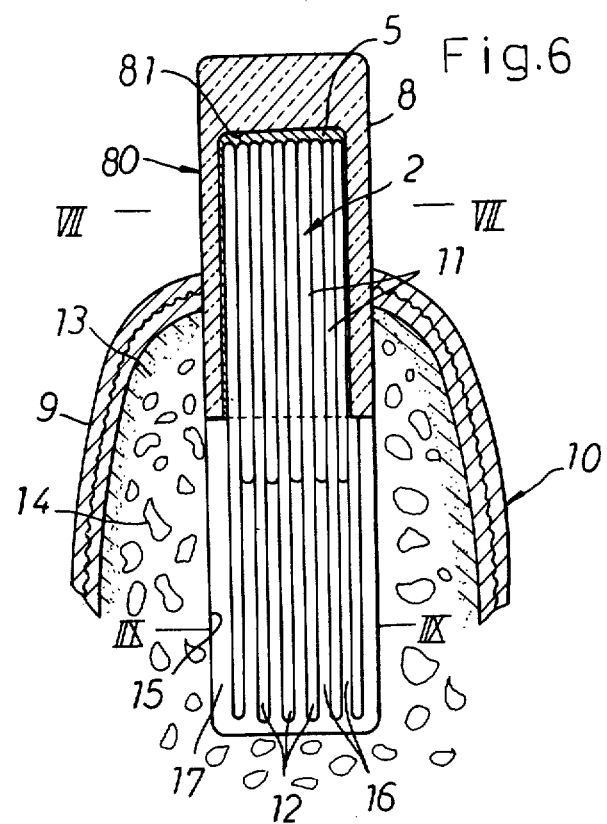
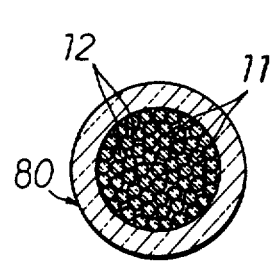 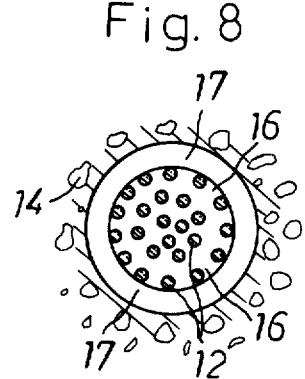

FLEXIBLE CERAMIC BIO-IMPLANT MEMBER

This is a continuation, of application Ser. No. 100,059, filed Dec. 4, 1979, now abandoned.

BACKGROUND OF THE INVENTION

1. Field of the Invention

This invention relates to a flexible ceramic bio-implant member and more particularly to a flexible ceramic bio-implant member designed to make effective redintegration of joints, bones, and teeth by flexibly reinforcing the bio-implant member by embedding, in a living hard tissue to be redintegrated by a conventionally known bio-implant member, above all in the medullary cavity, a bundle of a plurality of flexible and elastic fibers unharmful to a living body (hereinafter referred to as a fiber bundled body) such as ceramic fibers, glass fibers, carbon fibers, silicon carbide fibers and other flexible and elastic fibers free from harmful effects on the living body.

2. Prior Art

The present applicant has heretofore provided numerous inventions and devices related with various types of implant members made of a ceramic material which has good affinity with the bony tissue and has no toxicity and which is chemically and physically stable in a living body and also high in mechanical strength. For example, a ceramic screw implant member and a ceramic blade implant member for use in dental treatment, and a ceramic bone joint, a ceramic bone screw, a ceramic hip joint and the like for use in orthopedic treatment may be mentioned as some of the examples of such inventions and devices. The members used in the prior inventions and devices mentioned above, however, have been made solid in their entire configuration by a close or a porous material or a close and porous material, and consequently the members of the type described are not free from that weakness in impulsive force which is a drawback inherent in ceramics nor free from brittleness due to paucity of flexibility. This fact provides a possibility that the implant members, when used within or around the bone, may be unable to follow the deformation of the bone due to the movement of the human body, depending upon the region in which the implants are used, and may be broken or may damage the bone around the members due to microcracks liable to be produced on the surface of the members themselves, which possibility, in turn, constitutes a major factor in making the members relatively restrictive in their range of applicability.

SUMMARY OF THE INVENTION

Accordingly, this invention has for its object the provision of a ceramic implant member free from the disadvantages inherent in the prior art ceramic implant members which were inflexible and fragile. As will become obvious from three animal experiments and examples of clinical tests on men that will follow, the bone portion restored to a normalcy by combined use of the flexible implant member of the invention and the prior art ceramic implant member has been not only satisfactory in post-operation redintegration but can sufficiently adapt itself to the normal activities of the men and animals operated. Because the member provided by the invention consists mainly of a bundled body of flexible and elastic fibers unharmful to a living body and because the bundled body is held in the state of most of its longitudinal fibers being allowed to make flexible movement with respect to one another except the relatively narrow and mutually bound portion extending in the longitudinal direction of the bundled body and is inserted into and embedded in the redintegrated bone, the body forms a flexible sone in contact with the inside of the bone and permits the infiltration, proliferation, and growth of a new bone in the microgap between the fibers or in the microgap purposely formed between the inside of the bone and the fibers. The construction of the member described above makes it possible that, when an external force imparted to the redintegrated region works in the form of concentrated stress on the ceramic implant member which can only rigidly respond to the force, the flexible deformation and elastic returning of the fiber bundled body (including a new bone) inside the bone disperse and absorb the external force to reduce the force and thereby can prevent the brittle fracture of the implant member and damage of the bone and can also help the growth of the bone. As component fibers of the fiber bundled body used in the invention may be mentioned such inorganic fibers unharmful to a living body and having both flexibility and elasticity as for example, preferably, alumina monocrystalline fiber, namely, a fiber obtained by drawing an α-alumina melt upwardly through a specified gap structure and growing the alumina monocrystals in the melt in the direction of C-axis crystal, the fibers thus obtained being on the order of less than 1 mm, preferably 0.1–0.5 mm and less than 2 mm in diameter respectively in the case of a solid fiber and in the case of a tubular fiber. Although ceramics in property, this fiber has in itself a suitable degree of flexibility and elasticity and is markedly superior in mechanical strength. As other fibers having similar aptitude may be mentioned a glass fiber, silicon carbide fiber, carbon fiber, etc. which, as well known, are commercially readily available. The diameter of such a fiber must properly be determined in consideration of the properties of the fiber and also in consideration of flexibility and elasticity necessary for the region in which the fiber is used. Namely, in view of the characteristic of locomotion inherent in the bone in the region to be reinforced by the fiber bundled body, it is desirable to use a multiplicity of fibers comparatively small in diameter when high flexibility is required, and conversely, the use of a small number of fibers comparatively large in diameter is suitable for the purpose for which low flexibility and reinforcement adapted for support are required. The bundled body in principle consists entirely of fibers over the whole range of its diameter but, as shown in one of its modified forms to be described hereinafter, the fibers of the bundled body may be arranged only in the range of certain thickness extending from the region in which they come in contact with the inside of the bone toward the center of the body and in the region more approximate to the center than that range may be arranged a core made of different ceramics and having a desired shape such as a rod, tube or a longitudinal cavity corresponding to the core may be formed in the center of the fiber bundled body arranged in a ringlike manner so as to permit the range of flection of the fibers constituting the bundled body to extend into the cavity. The invention also includes this type of modification. Such a modification is conveniently employed in combination in accordance with the type of reinforcement required of the portion to be redintegrated, but the object of the invention makes it necessary to arrange the fiber bundled body at least in the region inside of the bone to be redintegrated. As previously described, this fiber bundled body is inserted into and embedded in the bone and particularly in the medullary cavity with most of the longitudinal part of the bundled body maintained in the state of not being bonded to one another but being allowed to make free flexible movement. In-sertion of the body into the medullary cavity provides no functional disadvantage at all in the case of a living body whose growth of bone is arrested.

BRIEF EXPLANATION OF THE DRAWINGS

A detailed description will now be given of four preferred embodiments of the invention with reference to the accompanying drawings.

In the drawings:

FIG. 4 is a longitudinal sectional front view of a second embodiment of the invention in the bone joint of a broken part of a long trunk bone of a large-size dog;

FIG. 5 is a sectional view taken along the line V—V of FIG. 4;

FIG. 6 is a longitudinal sectional front view of a third embodiment of the invention in an endosseous implant to be embedded in the mandible of a medium-size dog;

FIG. 7 is a sectional view taken along the line VII—VII of FIG. 6;

FIG. 8 is a sectional view taken along the line IIX—IIX of FIG. 6;

DETAILED DESCRIPTION OF THE PREFERRED EMBODIMENTS OF THE INVENTION

EXAMPLE 1

Figure 1:
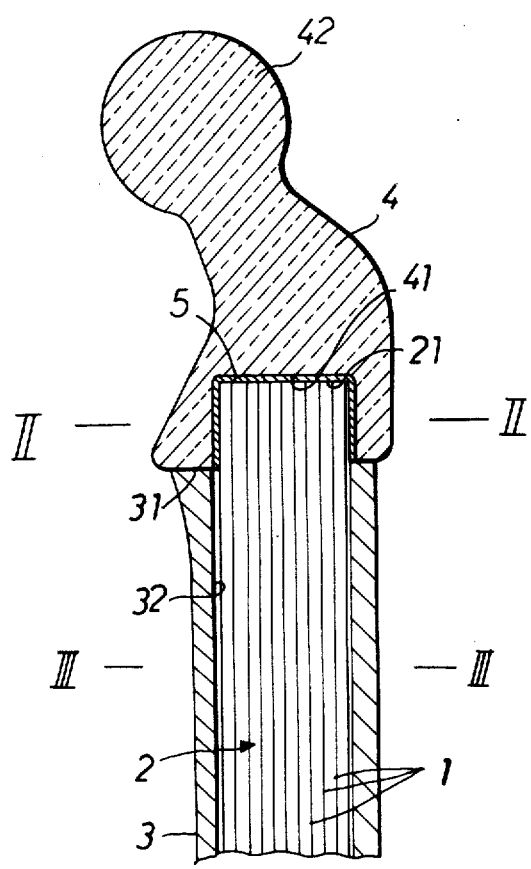
FIG. 1 is a longitudinal sectional front view of the essential part of a first embodiment of the invention in the condyle of an artificial hip joint of a sheep.
Figure 2:
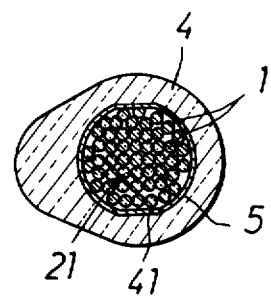
FIG. 2 is a sectional view taken along the line II—II of FIG. 1.
Figure 3:
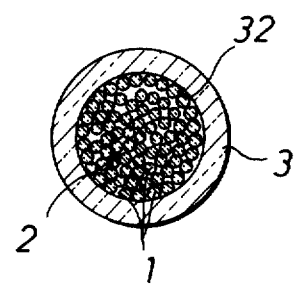
FIG. 3 is a sectional view taken along the line III—III of FIG. 1.

(a) Reference drawing: FIGS. 1 to 3

(b) Fiber bundled body:

A plurality of alumina monocrystalline fibers 1 . . . each having a diameter of about 0.5 mm were bundled into a cylindrically bundled body about 12 mm in diameter and about 54 mm in length.

(c) Portion redintegrated and method of redintegration:

In order to reinforce the joining of a top 4 of an artificial condyle to a proximal end of a thighbone 3 of a sheep, an upper end portion 21 of a fiber bundled body 2 was fitted into a cavity 41 formed in the lower portion of the joint 4 and powdered glass of a component approximate in thermal expansion characteristic to alumina and unharmful to a living body was interposed as a binding agent 5 between the end portion 21 and the bottom of the cavity 41 to melt the agent 5 to obtain fixation between the two by heating the powdered glass in an electric furnace (not shown) at a temperature higher than the melting point of the powdered glass. The artificial hip joint 4 was obtained by forming a bulk of alumina monocrystals (or a sintered body of alumina ceramic polycrystals instead of a bulk of alumina monocrystals may be used) and was provided on the top with a condyle 42. The exposed portion except the inside of the cavity 41 of the fiber bundled body 2, namely, a stem portion of the artificial condyle was directly inserted from the cutout portion 31 of a thighbone 3 in the longitudinal direction into a medullary cavity 32.

(d) Post-operation results:

The joint portion was left fixed by gypsum for two weeks after the operation in (c), and after a lapse of two months thereafter the joint portion was subjected to X-ray inspection, to find that a new bone tissue proliferated in the microgaps between the fibers of the fiber bundled body 2 and around the fiber bundled body 2, and joining of the body 2 to the thighbone 3 was satisfactory and that the sheep was restored to such an extent that it could walk in a normal manner. The region operated was under satisfactory restoration. By the way, the conventional method used for restoring the same region was such that the artificial condyle was made of stainless steel or a Co-Cr-Mo alloy and a stem adapted to be inserted into the medullary cavity was integrally formed to project downwardly on the lower portion of the condyle. Accordingly, such an artificial condyle lacked affinity with the thighbone in point of material and direct fixation of the bone joint to the thighbone was impossible. Therefore, it was a general practice to mix, paste bone cement (chiefly methyl methacrylate cement) hardenable at normal temperature in a known manner, pour the cement into the medullary cavity in a paste state (before getting hardened), then insert the stem into the cavity, and harden the cement after the gap between the inside wall of the bone and the stem has been filled. In this case, because so-called absorption of bone was effected by the heat produced in time of the cement setting, change in property due to effect of time, and the toxicity of humorsoluble nonpolymer left in the cement, the condyle of the thighbone and especially the stem portion of the thighbone got loosened. This was a great disadvantage. In contrast thereto, because in the invention the flexibility and elasticity of the fiber bundled body provide good contact between the inside wall and the stem and further because the bone grows within the thighbone, the gap between the inside wall and the stem is fully filled, with the result that complete fixation is effected between the fiber bundled body and the thighbone. On the other hand, since the invention is not harmful to a living body unlike the relation between the metal and the bone cement, the post-operation results are also satisfactory, and the flexibility with which the bundled body can follow movement of the bone provides a state in which the body is liable to become affinitive with the bone. The invention is greatly improved in this respect.

EXAMPLE 2

(a) Reference drawing: FIGS. 4 to 5.

(b) Fiber bundled body:

Alumina monocrystalline fibers 1 of about 0.1 mm in diameter were cylindrically bundled into a fiber bundled body 2 of about 5 mm in diameter and about 50 mm in length.

(c) Region redintegrated and method of redintegration:

In order to reinforce the prosthesis of the broken region of the long trunk bone 7 (shin of a hind leg) of a large-sized dog weighing 25 kg, a ringshaped joint 6 made of porous ceramics about 0.2 mm in pore diameter and corresponding to the bone configuration of the broken region was prepared. The fiber bundled body 2 was inserted through the joint 6, and bone cement 5 of methyl acrylate was interposed in the gap between the body 2 and the joint 6. In order to make the cement 5 innoxious, the cement, after it set, was heated for 30 minutes at temperatures in the range of room temperature to 60° C., then for one hour at 60° C., further for 30 minutes up to 100° C., and for 30 minutes at 100° C. and left to stand in physiological saline solution for 24 hours at normal temperature after having been cooled. As a result, substantially no rendering of a water-soluble component in the cement was noticed. Next, in order to practise prosthesis on a defect of the bone 7 by the fiber bundled body 2 gripped in substantially the middle part of the joint 6, the defect of the long trunk bone 7 was excised over a length of about 20 mm longitudinally of the bone, and the fibers of the body 2 projecting beyond the upper and lower sides of the joint 6 were longitudinally inserted into and embedded in the respective medullary cavities 71, 71 of split-apart upper and lower trunk bones 7, 7.

(d) Post-operation results:

After operation in (c), the affected part was fixed with gypsum for three weeks and thereafter the gypsum was removed. An X-ray examination showed that the joining of the region operated was satisfactory and that nothing was the matter with the walking ability of the operated dog whose post-operation course was normal.

EXAMPLE 3

(a) Reference drawing: FIGS. 6, 7 and 8

(b) Fiber bundled body:

Alumina monocrystalline fibers 1 having a mean diameter of 0.25 mm were cut in two ways in a length of 12 mm and in a length of 20 mm, combined alternately in short and long lengths so as to be arranged even at one end and a cylindrical fiber bundled body 2 of a diameter of 3 mm was obtained. In the drawing, the numeral 11 designates short fibers and 12 designates long fibers. The upper half of the fiber bundled body 2 shown in the drawing is closely filled with short and long fibers 11 and 12, but the bundle body 2 is formed in the lower half with fiberlike macrogaps 16 lacking in short fibers and extending over a length of 8 mm and are filled coarsely with long fibers 12.

(c) Region redintegrated and method of redintegration:

In order to form a dental root portion for a dental endosseous implant for a medium-size dog weighing about 15 kg in body weight, an implant post 8 made of a compact alumina ceramic sintered body and 4 mm in diameter and 13 mm in length and having a cavity 81 closed on the top and measuring 3 mm in diameter and 10 mm in depth was made in advance, and the bundled body 2 was inserted into the cavity 81 from an open end of the cavity 81 through the same cement as that in Example 1 and fixed to the bottom of the cavity, to obtain a pin implant 80 havig the fiber bundled body as a core. On the other hand, a vertical cavity 15 having a diameter of 4 mm and a depth of 15 mm was formed in the mandibular bone 10 of the dog, the cavity extending through a gingival mucous membrane 9, hard bone tissue 13 and spongy matter portion 14. Thereafter, the implant 80 was set in the cavity 15. As a result, the longer fibers 12 out of the fiber bundled body 2 were inserted from a position about 3 mm below the surface of the hard bone tissue 13 deep into the spongy matter portion 14 of the mandibular bone 10.

(d) Post-operation results:

For about 10 days after the implant in (c) was over, the gingival mucous membrane 9 was firmly attached to the surface of the ceramic implant 80, and 20 days thereafter, proliferation and filling of a new bone were noticed in the gap 17 between the cavity 15 and the long fibers 12 and in the gap 16 between the fibers. An upper structure (not shown) corresponding to a tooth crown portion of the dog was made by use of platinum-added gold (Au-Pt alloy) on the upper projecting portion 18 (projecting portion within the mouth) of the ceramic implant 80 and the upper structure was adhered by dental cement to the upper projecting portion 18 to provide normal occlusion. Nothing unusual was observed one year thereafter and normal occlusion is practised. When long and short fibers are used as shown in this example, infiltration, proliferation, and growth of a new bone are regionally enlarged and accordingly, holding power with respect to the implant is increased and dispersion and absorption of stress from the upper and lateral sides becomes vigorous.

EXAMPLE 4

(a) Reference drawing: FIGS. 9 to 12

(b) Fiber bundled body:

A bundled body of hollow alumina ceramic monocrystalline fibers 1 . . . oval in section obtained by a molten salt drawing method so as to have a major axis of 1.5 mm and a minor axis of 1.0 mm with a c-axis in a longitudinal direction.

(c) Region redintegrated and method of redintegration:

In order to join the fractured and broken regions 19, 20 of a forearm bone (radius) 18 of the human body, a rodlike spacer 23 of alumina ceramics (a cap 22 and the spacer 23 were enlarged in a trumpet shape respectively on the rear side so as to improve contact of a bone 18 with the fibers 1 . . . to be later described) was adhered substantially concentrically by bone cement 5 to the center of an alumina ceramic cap 22 and the monocrystalline fibers 1 . . . were inserted in three layers into the ringlike gap between the spacer 23 and the cap 22 so as to permit the major axes of the fibers 1 . . . to extend close to the bone along the circumference of the bone and were bound and fixed between the fibers 1 . . . themselves, between the cap 22 and the thus fixed fibers, and between the cap 22 and the spacers 23 through bone cement 5 to provide a fiber bundled body 2 bundled at the distal end portion of the fibers 1 . . . by the cap 22. The fibers 1 . . . were cut at the rear end in uniform lengths of about 200 mm, and preferably, in order to evade an unnecessary impetus to a living body, the fibers 1 . . . might be bundled and bound by a separate cap (not shown).

Figure 9:
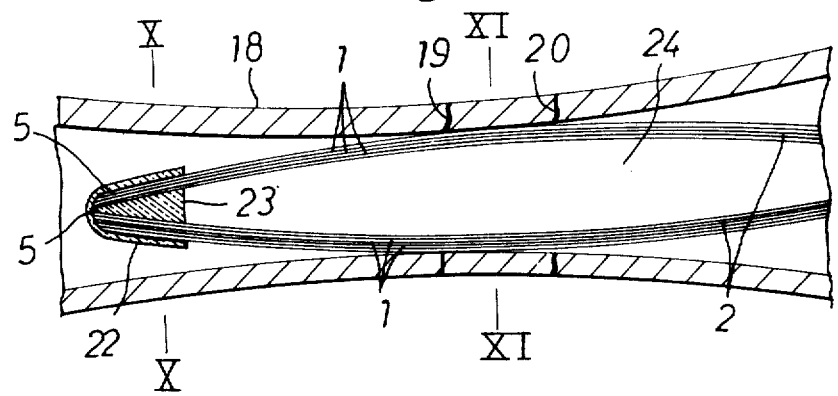
FIG. 9 is a longitudinal sectional front view of a fourth embodiment of the invention in the joint prosthesis of the fractured and broken region of a forearm bone of the human body.
Figure 10:
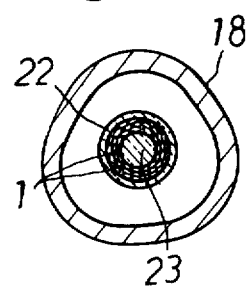
FIG. 10 is a sectional view taken along the line X—X of FIG. 9.
Figure 11:
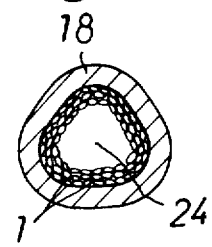
FIG. 11 is a sectional view taken along the line XI—XI of FIG. 9.
Figure 12:
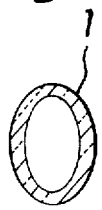
FIG. 12 is an enlarged cross-sectional view of a fiber.

Next, the fiber bundled body 2 was inserted through the medullary cavity from the proximal side to the distal side of the radius 18 and, as shown in FIG. 9, the fibers 1 . . . were stopped so as to be brought into contact with the inner wall of the bone 18 in substantially the middle of the lengths of fibers 1 . . . (the broken region and its neighborhood).

By so doing, high longitudinal flexibility which Examples 1 to 3 lacked was imparted to the fibers 1 . . .

themselves with respect to the direction (centripetal) of the cavity 24 because the fibers 1 . . . were not brought into contact with each other with respect to the longitudinal range corresponding to the diameter of the spacer 23 but were longitudinally arranged within the medullary cavity with a slender cavity 24 maintained with respect to the longitudinal range. At the same time, because the fibers 1 . . . were used which were by themselves oval in section and hollow, they were high in flexibility with respect to their major axes and low in flexibility with respect to their minor axes. This fact is the reason why the above arrangement of minor axes makes it possible for the fibers 1 . . . to fully absorb the force working in the direction of bending the bone 18 through flection of the fibers in the direction of minor axes and why the above arrangement conversely makes it possible for the fibers to resist the force working in the direction of major axes (for example, torsional force) by low flexibility (more or less rigidity comes out). The fact that the fibers 1 . . . are hollow provides also flexibility in the direction of minor axes of the fibers in addition to the above flexibility.

Thus, according to this example, in addition to high flexibility in the form of a fiber bundled body, flexibility per piece of fiber is also increased, so that the bundled body is greatly improved in the characteristic of contact and in affinity with the bone. Consequently, after an operation, there is no need of applying compression plates to the joined region of the bone 18. A desirable post-operation result as seen below can be obtained merely by the prosthetic method described above.

(d) Post-operation results:

Radiographic examination of the operated region two to three months after operation in (c) showed that the fractured and broken regions were not only completely united but also the fiber bundled body 2 was held in the marrow and adhesion of the body 2 to the bone was satisfactory and the post-operation course was thus quite normal.

Furthermore, as seen from bone-joining in this example, the invention makes it unnecessary to use compression plates to thereby render it unnecessary to undergo an operation for removing the plates, and accordingly the invention can prove a great boon to persons of advanced age and to hemophilic patients.

The above description has been given of this invention with reference to preferred embodiments of the invention but it should be understood that various modifications of the invention may be made as will be described below.

(I) As stated above, when the fiber is too small in diameter or the fiber itself is too elastic in proportion to its diameter and appears lacking in its holding strength when the fiber bundled body was implanted, the fiber bundled body is used in a ringlike manner only over an area in contact with the bone or over a range of certain thickness from the area in contact to the inside of the fiber bundled body and a complex bundle body containing a reinforcing ceramic core as a core material is used inside of the ringlike arranged fiber bundled body. But in this case the core should not be so rigid as to make it impossible for the bone to flex.

(II) The shape, size, flexibility, and elasticity of the fiber bundled body are changed by combining the fibers of different diameters with one another in accordance with the change of the inside shape of the bone in the region to be redintegrated.

(III) Further change is caused in the area of proliferation of a new bone by making more than three kinds of change in the length of fiber.

(IV) A combination of (II) and (III) is carried out.

(V) Change in the area of diametrical distribution of flexibility in the fiber bundled body is effected by a combination of fibers of different properties. A combination of (V) with (II), (III) and (VI) may be carried out.

(VI) The sectional shape of the fiber, in addition to oval and round shapes described by example, may conveniently be of any of triangle, square and polygon.

(VII) The invention may find its wide application in the redintegration and prosthesis of bones, joints, and teeth in the areas other than the illustrated regions adapted to be redintegrated by orthopedic and dental treatment insofar as the application lies within the scope of the invention.

As will be understood from the description above, the invention is highly useful in that the invention makes it possible for a bundled body of fibers flexible, elastic, and unharmful to a living body to find its application as a flexible reinforcing body for an implant inside of the bone in the state of the bundled body being allowed to make flexible movement approximate to the movement of the bone without the fibers basically being bound to each other with respect to most of the longitudinal direction of the fibers and that it further makes it possible for a new bone tissue to infiltrate into and proliferate and grow in the macrogaps in the bundled body. Accordingly, as illustrated in the embodiments, dispersion and absorption of an outer force in the redintegrated regions are excellent, and the impulse fragility which was a weak point of ceramic implants heretofore in use, namely, breakage of the entire implant due to a local surface defect such as microcracks liable to be produced on the surface of the implant and the resulting breakage of the living bone are greatly reduced by the fiber bundled body. The invention is thus predominantly effective for increasing the aptitude of a ceramic implant member.

We claim:

1. A flexible bio-implant member comprising a bundled body of a plurality of longitudinally arranged fibers having flexibility and elasticity and bundled into a desired shape in the state of the fibers being allowed to make flexible movement, wherein the length of each fiber extends in substantially the same longitudinal direction and said fiber bundled body is adapted for permanent insertion into the bone of a living body to be joined or redintegrated by the bio-implant member, wherein the fibers are arranged to define gaps therebetween which are sufficiently small so that new bone tissue will grow in the gaps and wherein the fibers have sufficient length so that they extend across a joint portion of the bone to be joined or redintegrated.

2. A member according to claim 1 wherein said fiber bundled body has a configuration adapted to fit into the medullary cavity of the bone of a living body and is adapted to be placed in the bone so that its outer circumference is in contact with the inside surface of the bone and is bound and bonded at least in a portion of the bundled body with said flexible bio-implant member by a bonding agent unharmful to the living body.

3. A member according to claim 1 wherein each fiber of said fiber bundled body is substantially the same in length.

4. A member according to claim 1 wherein the fibers constituting said fiber bundled body consists of a plural kinds of fibers respectively different in lengths, said fibers forming a plurality of fiberlike macrogaps produced in the bundled body by the portions lacking in fibers because of unequal lengths between short and long fibers when the fibers are bundled into a desired shape.

5. A member according to claim 1 wherein fibers of said fiber bundled body are selected from fibers each 1 mm in diameter or from a plural kinds of fibers whereby the configuration, size, flexibility and elasticity of said fiber bundled body are brought into correspondence with the function of the bone of said living body and the internal configuration of the fiber bundled body.

6. A member according to any one of claims 1 to 5 wherein said fibers are selected from alumina monocrystalline fibers, glass fibers, carbon fibers, and silicon carbide fibers.

7. A member according to claim 1 wherein said fibers each are less than 1 mm in diameter and are of a solid body.

8. A member according to claim 1 wherein said fiber bundled body is substantially cylindrical in shape.

9. A member according to claim 2 wherein said fiber bundled body consists of a core such as a rod, tube, ring, and the like, and of a substantially ringlike fiber bundled body having its component fibers arranged outside of said core.

10. A member according to claim 2 wherein said fibers are oval in section.

11. A member according to claim 7 wherein said fibers are between 0.1 and 0.5 mm in diameter.

12. A member according to claim 5 wherein said fibers are tubular alumina crystalline fiber less than 2 mm in diameter.

13. A member according to claim 1 wherein said fiber bundled body has a configuration adapted to fit into a cavity artificially formed in the bone.

14. A flexible bio-implant member comprising a bundled body of a plurality of longitudinally arranged substantially coextensive fibers having flexibility and elasticity and bundled into a desired shape in the state of the fibers being allowed to make flexible movement, wherein the length of each fiber extends in substantially the same longitudinal direction and said fiber bundled body is adapted for permanent insertion into the bone of a living body to be joined or redintegrated by the bio-implant member, wherein the fibers are arranged to define gaps therebetween which are sufficiently small so that new bone tissue will grow in the gaps.

* * * * *